(12) United States Patent
Kawanishi et al.

(10) Patent No.: US 7,812,155 B2
(45) Date of Patent: Oct. 12, 2010

(54) PROCESS FOR PREPARING AN O-ALKYLATED RAPAMYCIN DERIVATIVE AND O-ALKYLATED RAPAMYCIN DERIVATIVE

(75) Inventors: Tetsuro Kawanishi, Kanagawa (JP); Masashi Isozaki, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 84 days.

(21) Appl. No.: 11/984,988

(22) Filed: Nov. 26, 2007

(65) Prior Publication Data

US 2008/0146796 A1 Jun. 19, 2008

Related U.S. Application Data

(60) Provisional application No. 60/861,249, filed on Nov. 28, 2006.

(30) Foreign Application Priority Data

Nov. 27, 2006 (JP) .............................. 2006-318901

(51) Int. Cl.
*C07D 498/18* (2006.01)
(52) U.S. Cl. ..................................... 540/456
(58) Field of Classification Search .................. 540/456
See application file for complete search history.

(56) References Cited

U.S. PATENT DOCUMENTS

| 6,328,970 | B1 | 12/2001 | Molnar-Kimber et al. | |
|---|---|---|---|---|
| 7,220,755 | B2 * | 5/2007 | Betts et al. | 514/291 |
| 2005/0192311 | A1 | 9/2005 | Isozaki et al. | |

FOREIGN PATENT DOCUMENTS

| JP | 9-512018 A | 12/1997 |
|---|---|---|
| JP | 2000-510815 A | 8/2000 |
| JP | 2004-149542 A | 5/2004 |
| JP | 2005-281296 A | 10/2005 |
| WO | WO 94/09010 A1 | 4/1994 |
| WO | WO 94/25022 A1 | 11/1994 |
| WO | WO 95/28406 A1 | 10/1995 |
| WO | WO 96/41807 A1 | 12/1996 |
| WO | WO 2005/010010 A1 | 2/2005 |
| WO | WO 2006/069333 A1 | 6/2006 |

OTHER PUBLICATIONS

Nickmiler et al. (Clinical Chemistry (Washington, D. C.) (1998), 44(3), 532-538).*
Search Report for corresponding application No. PCT/JP2007/072062, dated Dec. 18, 2007, in the Japanese language.
L.A. Sorbera et al., "SDZ-RAD," Drugs of the Future 1999, pp. 22-29, vol. 24, No. 1, Prous Science.

* cited by examiner

*Primary Examiner*—Bruck Kifle
(74) *Attorney, Agent, or Firm*—Buchanan Ingersoll & Rooney PC

(57) ABSTRACT

A process for preparing an o-alkylated rapamycin derivative represented by the following general formula (1) is provided. The process includes the steps of reacting rapamycin with an alkyl triflate, purifying the resulting reaction product with a normal phase chromatograph and further purifying a purified product, which has been purified with the normal phase chromatograph, with a reverse phase chromatography (1)

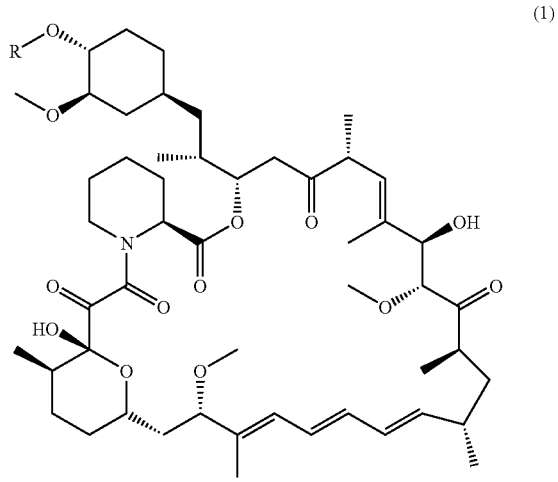

wherein R represents an alkyl, arylalkyl, hydroxyalkyl, alkoxyalkyl, acyloxyalkyl, aminoalkyl, alkylaminoalkyl, alkoxycarbonylaminoalkyl, acylaminoalkyl, or aryl.

15 Claims, 2 Drawing Sheets

PROCESS FOR PREPARING AN O-ALKYLATED RAPAMYCIN DERIVATIVE AND O-ALKYLATED RAPAMYCIN DERIVATIVE

CROSS-REFERENCE TO RELATED APPLICATION

This application claims the benefit of priority of U.S. Provisional Application No. 60/861,249 filed Nov. 28, 2006, the contents of which are incorporated herein by reference.

BACKGROUND

1. Field of the Invention

This invention relates to a process for preparing an o-alkylated rapamycin derivative of high purity and also to an o-alkylated rapamycin derivative prepared by the process.

2. Description of the Related Art

Rapamycin is a macrolide antibiotic produced from *Streptomyces hygroscopicus*. It has been reported that rapamycin has immunosuppressive action and also has anticancerous and antifungal activities. Because of these useful pharmaceutical activities, much has been reported about rapamycin derivatives (see Drugs of Future 1999, 24(1): 22 to 29).

On the other hand, for the synthesis of rapamycin derivatives, there has been disclosed, for example, in WO94/09010, a process of preparing an o-alkylated rapamycin derivative by reaction between rapamycin and an alkyl triflate in toluene solvent in the presence of lutidine. In WO94/09010, no mention is made of the yield or purity of the resulting o-alkylated rapamycin derivative. We made an additional test, with the result that the yield was as low as 23% and the purity was at about 92 to 95%.

A process of synthesizing an o-alkylated rapamycin derivative improved by us has been proposed in US2005/0192311A1. In US2005/0192311A1, a process is disclosed wherein rapamycin and an alkyl triflate are reacted in methylene chloride solvent in the presence of N,N-diisopropylamine and the compound obtained by the reaction is purified by a normal phase chromatograph. Although the yield could be remarkably improved according to the process of US2005/0192311A1, the purity of the resulting o-alkylated rapamycin was as low as about 95% (see Comparative Example of this specification).

In general, the purity of drugs may be a very important factor with respect to relative merits for use as a bulk drug powder. Low purity indicates that a large amount of impurities are contained, and is judged as having a low reliability from aspects of medical efficacy and safety. In case those having such a low impurity are used as a bulk drug powder, identification and quantitative determination of impurities and safety tests of impurities have been needed, with the attendant problem of increasing a risk and cost of development. Accordingly, it is very advantageous in product development to obtain a bulk drug powder of high purity.

SUMMARY

According to exemplary aspects, provided are a process for preparing an o-alkylated rapamycin derivative of high purity and an o-alkylated rapamycin derivative prepared by the process.

Exemplary aspects of such process and derivative are described in (1) to (18) below.

(1) A process for preparing an o-alkylated rapamycin derivative represented by the following general formula (1), including the steps of reacting rapamycin with an alkyl triflate, purifying the resulting reaction product with a normal phase chromatograph and further purifying a purified product, which has been purified with the normal phase chromatograph, with a reverse phase chromatograph,

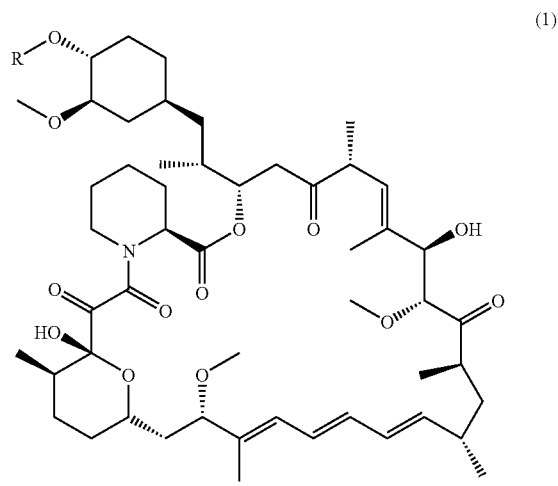

(1)

wherein R represents an alkyl, arylalkyl, hydroxyalkyl, alkoxyalkyl, acyloxyalkyl, aminoalkyl, alkylaminoalkyl, alkoxycarbonylaminoalkyl, acylaminoalkyl, or aryl.

(2) A process for preparing an o-alkylated rapamycin derivative as recited in (1), characterized in that a stationary phase used in the reverse phase chromatograph is made of a silica gel having a particle size of 5 to 100 μm and modified with at least one selected from an alkyl group, a phenyl group, and an alkylsilyl group.

(3) A process for preparing an o-alkylated rapamycin derivative as recited in (2), characterized in that the alkyl group is at least one member selected from a butyl group, an octyl group and an octadecyl group.

(4) A process for preparing an o-alkylated rapamycin derivative as recited in (2) or (3), characterized in that the particle size of the silica gel ranges 10 to 50 μm.

(5) A process for preparing an o-alkylated rapamycin derivative as recited in (1), characterized in that an eluent used in the reverse phase chromatograph is a mixed solution obtained by mixing 10 to 50 vol % of water relative to at least one organic solvent selected from acetonitrile, methanol, ethanol and propanol.

(6) A process for preparing an o-alkylated rapamycin derivative as recited in (5), characterized in that the organic solvent is acetonitrile or methanol.

(7) A process for preparing an o-alkylated rapamycin derivative as recited in (6), characterized in that a ratio of the water to the acetonitrile or methanol ranges 20 to 35 vol %.

(8) A process for preparing an o-alkylated rapamycin derivative as recited in (1), characterized in that an infusion fluid used in the reverse phase chromatograph is a mixed solution obtained by mixing 40 to 60 vol % of water relative to with at least one organic solvent selected from acetonitrile, methanol, ethanol and propanol.

(9) A process for preparing an o-alkylated rapamycin derivative as recited in (1), characterized in that a product purified by the normal phase chromatograph in an amount of 1 to 4 g per 1.0 liter of a column head capacity is provided for separation in the reverse phase chromatograph.

(10) A process for preparing an o-alkylated rapamycin derivative as recited in any one of (1) to (9), characterized in that after the preparation of the o-alkylated rapamycin derivative according to the process recited in any one of (1) to (9), the resulting derivative is subsequently charged into a mixed solvent containing at least one solvent miscible with water and water, or is dissolved beforehand in at least one solvent miscible with water and charged into water or a mixed solvent containing water, thereby causing the product to be precipitated.

(11) A process for preparing an o-alkylated rapamycin derivative as recited in (10), characterized in that the solvent miscible with water is used at a ratio by weight of 2 to 10 relative to the o-alkylated rapamycin derivative.

(12) A process for preparing an o-alkylated rapamycin derivative as recited in (10) or (11), characterized in that the water is used at a ratio by weight of not less than 10 relative to the o-alkylated rapamycin derivative.

(13) A process for preparing an o-alkylated rapamycin derivative as recited in any one of (10) to (12), characterized in that the solvent miscible with water is an alcohol.

(14) A process for preparing an o-alkylated rapamycin derivative as recited in (13), characterized in that the alcohol is methanol.

(15) A process for preparing an o-alkylated rapamycin derivative as recited in (10) to (14), characterized in that the precipitation is performed such that the o-alkylated rapamycin derivative is dissolved beforehand in a solvent containing at least one solvent miscible with water, followed by charging into water or a mixed solvent of at least one solvent miscible with water and water.

(16) A process for preparing an o-alkylated rapamycin derivative according to (1), wherein a purity of the further purified product is not lower than 99%.

(17) An o-alkylated rapamycin derivative prepared by the process according to any one of (1) to (16).

(18) An o-alkylated rapamycin derivative according to (17), wherein a purity of the o-alkylated rapamycin derivative is not lower than 99%.

According to exemplary aspects, it becomes possible to prepare an o-alkylated rapamycin derivative having a high purity, for example, a purity of not lower than 99%.

DETAILED DESCRIPTION

Figure 1:
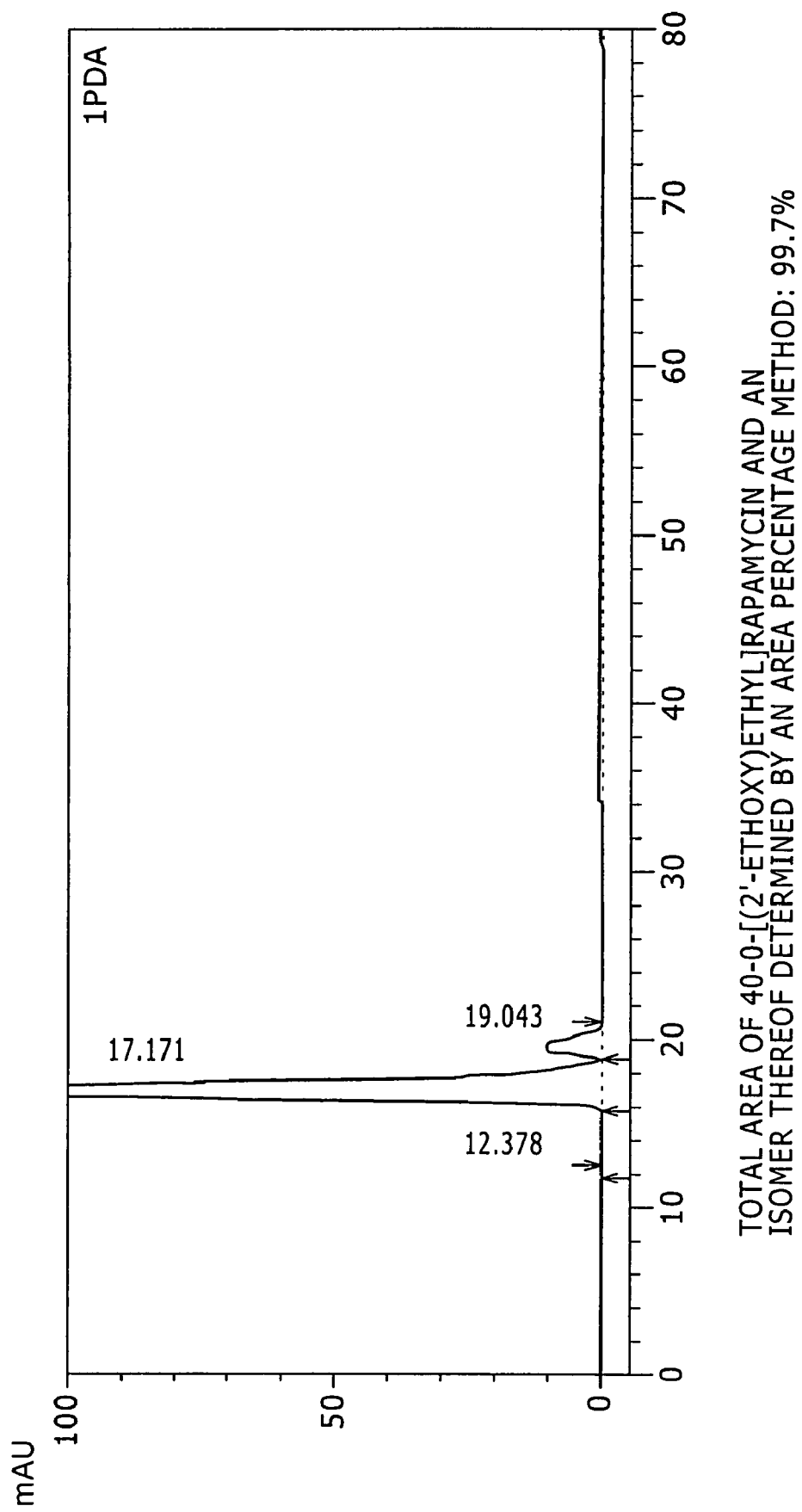
FIG. 1 is a chromatogram of a product obtained in Example 1.

The invention is now described more particularly. According to one aspect, a process for preparing an o-alkylated rapamycin derivative of the following general formula (1) is provided, characterized by including the steps of reacting rapamycin with an alkyl triflate, purifying the resulting reaction product with a normal phase chromatograph and further purifying a purified product, which has been purified with the normal phase chromatograph, with a reverse phase chromatograph.

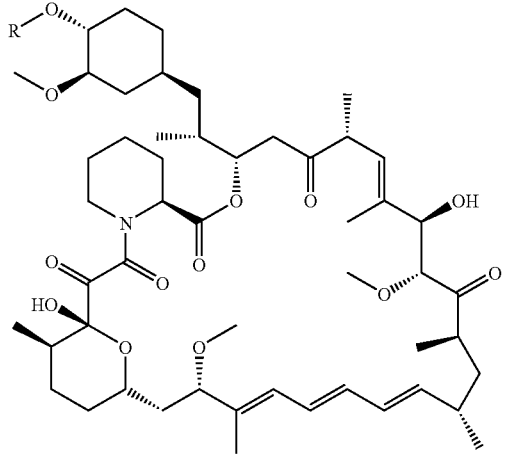

wherein R represents an alkyl, arylalkyl, hydroxyalkyl, alkoxyalkyl, acyloxyalkyl, aminoalkyl, alkylaminoalkyl, alkoxycarbonylaminoalkyl, acylaminoalkyl, or aryl.

For specific examples of the o-alkylated rapamycin derivative of the general formula (1) wherein R=alkoxyalkyl, there can be exemplified o-(2-ethoxyethyl)-rapamycin represented by the following formula (2) and the like.

O-(2-ethoxyethyl)-rapamycin can be obtained by reacting rapamycin with 2-ethoxyethyl triflate, which is a kind of alkyl triflate, for example, in the presence of N,N-diisopropylethylamine in methylene chloride solvent.

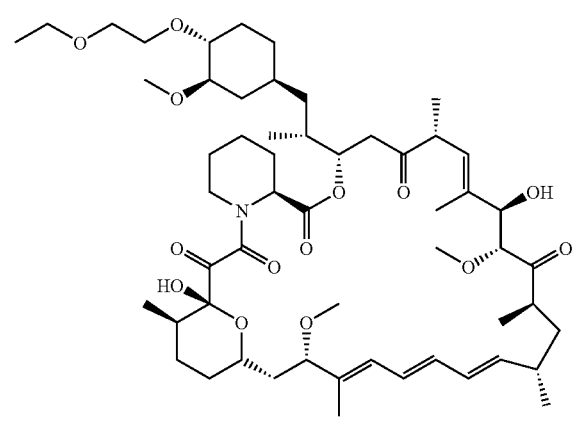

Specific examples wherein R=hydroxyalkyl include o-(2-hydroxyethyl)-rapamycin of the following formula (3) and the like.

O-(2-hydroxyethyl)-rapamycin can be obtained by reacting rapamycin with t-butyldimethylsilyloxyethyl triflate, which is a kind of alkyl triflate, for example, in methylene chloride solvent in the presence of N,N-diisopropylethylamine and deprotecting the t-butyldimethylsilyl group.

(3)

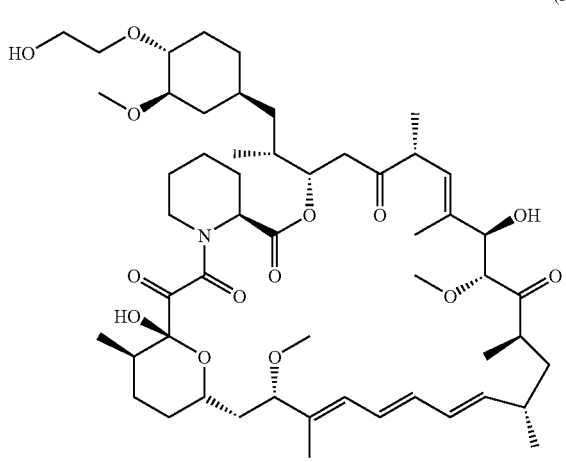

The solvents used in the step of reaction between rapamycin and an alkyl triflate are not critical in type so long as they have a dissolving power against starting materials and a reaction product and preferably include halogen-containing organic solvents, more preferably chlorine-containing organic solvents and most preferably methylene chloride or chloroform.

After the reaction between rapamycin and an alkyl triflate as stated above, the reaction product is purified with a normal phase chromatograph and the purified product obtained by the purification with the normal phase chromatograph is further purified with a reverse phase chromatograph. In this way, there can be obtained through these purification steps an o-alkylated rapamycin derivative of a high purity, for example, a purity of not lower than 99%.

The purity used herein means a peak area percentage of an o-alkylated rapamycin derivative obtained by analysis with liquid chromatography under the following conditions. More particularly, the purity can be calculated according to the calculation formula of (peak area of o-alkylated rapamycin derivative×100)/(sum of all peak areas) and is indicated by a value by %.

(Conditions of Liquid Chromatograph)
  Column: Zorbax SB-C18, with 4.6 mm in diameter×25 cm in length (made by Agilent Technologies Co., Ltd.)
  Eluent: 70 vol % of acetonitrile/30 vol % of deionized water
  Infusion dose: 10 uL (10 mg of a sample dissolved in 20 ml of acetonitrile)
  Flow rate: 2.0 ml/minute • Analyzing time: 1 hour
  Detection: UV 278 nm • Column temperature: 40° C.

The normal phase chromatograph refers to a normal phase chromatograph ordinarily employed for analysis or purification by preparative separation. More particularly, the normal phase chromatograph is a separation system wherein the polarity of a stationary phase is higher than the polarity of a mobile phase. Silica gel or the like is used as the stationary phase and where silica gel is used as a stationary phase, sample molecules are adsorbed to a silanol group, followed by separation and purification through a adsorption-desorption process. For an eluent of the mobile phase, there is used a solvent with low polarity such as hexane, ethyl acetate, chloroform, or mixtures thereof.

The reverse phase chromatograph refers to a reverse phase chromatograph ordinarily employed for analysis or purification by preparative separation. More particularly, the reverse phase chromatograph is a separation system wherein unlike the normal phase chromatograph, the polarity of a mobile phase is higher than the polarity of a stationary phase. For the stationary phase, a particulate filler wherein the silanol group of silica gel is modified with a modification group to impart hydrophobicity thereto (hereinafter referred to as stationary phase particles) is used. For an eluent of the mobile phase, one having high hydrophilicity such as water, or a mixture of water and an organic solvent miscible with water, e.g., methanol, ethanol or acetonitrile is used. The stationary phase or a column filled with a stationary phase beforehand is commercially available from a number of makers and can be readily utilized. It will be noted that the properties of the stationary phase particles differ depending on the type of modification group, degree of modification, particle size, specific surface area, pore capacity and pore size and the like.

For a modification group modifying the stationary phase used in the reverse phase chromatograph, mention is made, for example, of an alkyl group, a phenyl group, and an alkylsilyl group. The alkyl group includes, for example, a butyl group, an octyl group or an octadecyl group. It will be noted that the alkyl group may be substituted at part thereof with other functional group and examples include a cyanopropyl group, an aminopropyl group, a pyrenylethyl group, a nitrophenylethyl group and the like. The phenyl group may also be substituted at part thereof with other functional group, and include, for example, a nitrophenyl group, a cyanophenyl group and the like. Moreover, the silanol group of silica gel may be modified at part thereof and the silanol group left unmodified may be end capped. Because the kind of modification group and the degree of modification influence the properties of the stationary phase, appropriate selection thereof suited for the purpose of separation is necessary while taking into account the properties of a compound to be separated and also other factors such as an eluent. It is to be noted that where an o-alkylated rapamycin derivative is purified, a butyl group, an octyl group or an octadecyl group is preferred as a modification group.

The stationary phase particles used in the reverse phase chromatograph are commercially available as having a particle size ranging from 3 μm to about 500 μm. In general, a smaller particle size leads to a more improved separation performance, but results in a higher resistance and a higher column pressure, for which a difficulty is involved in increasing a flow rate. In addition, a smaller particle size results in a higher cost. Accordingly, while taking required separability, amount of treatment, treating time and cost performance into consideration, an appropriate particle size should be selected depending on the purpose of purification. It will be noted that where the o-alkylated rapamycin derivative is purified, the particle size preferably ranges from 10 to 50 μm, more preferably 10 to 25 μm.

The eluent used in the reverse phase chromatograph is preferably a mixed solution obtained by mixing 10 to 50 vol % of water relative to at least one organic solvent selected from acetonitrile, methanol, ethanol and propanol. More preferably, the organic solvent is acetonitrile or methanol. Most preferably, the ratio of water to acetonitrile or methanol ranges from 20 to 35 vol %. It will be noted that the type of organic solvent and a mixing ratio with water should be appropriately selected depending on the type of stationary phase, a column capacity and an amount of separation.

The infusion fluid used in the reverse phase chromatograph is preferably a mixed solution obtained by mixing 40 to 60 vol % of water relative to at least one organic solvent selected from acetonitrile, methanol, ethanol and propanol. The product purified with the normal phase chromatograph is dissolved in such a mixed solution.

The amount of the stationary phase and the amount of a starting material (a product purified with the normal phase chromatograph) served for separation influences a purity and a collection rate of an intended purified product. For instance, where silica gel which is modified with at least one selected from a butyl group, an octyl group and an octadecyl group and whose particle size ranges 10 to 25 μm is used as the stationary phase and a mixed solution having a ratio of water of 20 to 35 vol % relative to acetonitrile or methanol is used as an eluent, 1 to 4 g of a starting material per 1.0 liter of a column head capacity is provided for separation. For example, when a column having an inner diameter of 5 cm and a length of 25 cm, 0.5 to 2 g of a starting material is provided for separation, when a column having an inner diameter of 20 cm and a length of 30 cm, 9.5 g to 38 g of a starting material is provided for separation, an o-alkylated rapamycin derivative of an intended high purity can be collected at a rate within a tolerable range.

The o-alkylated rapamycin derivative purified by means of the reverse phase chromatograph can be powdered by dissolving the o-alkylated rapamycin derivative in a solvent miscible with water and charging the resulting solution into water to cause the derivative to be precipitated. The powdering may also be possible by dissolving the o-alkylated rapamycin derivative in a mixed solvent containing at least one solvent miscible with water and water beforehand and allowing the resulting solution to stand for precipitation. Such powdering enables handling properties for use as a bulk drug powder to be improved along with improved quality stability and preservation stability. These merits contributes to manufacturing stability upon coating on a stent as will be described hereinafter.

The solvent, which is miscible with water and is used for powdering of the o-alkylated rapamycin derivative obtained according to an exemplary process, is preferably an alcohol, more preferably methanol.

The solvent, which is miscible with water and is used for powdering of the o-alkylated rapamycin derivative obtained according to an exemplary process, is preferably used at a ratio by weight, to the o-alkylated rapamycin derivative, of 2 to 10.

Water used for powdering of the o-alkylated rapamycin derivative obtained according to an exemplary process is preferably at a ratio by weight of not less than ten relative to the o-alkylated rapamycin derivative.

The o-alkylated rapamycin derivative obtained by an exemplary process is, for example, coated on medical instruments such as a stent. When the stent coated with the o-alkylated rapamycin derivative is placed in a lesion such as a blood vessel or the like, the o-alkylated rapamycin derivative is taken in the lesion to prevent restenosis.

EXAMPLES

The invention is illustrated by way of examples.

Example 1

(1) Preparation of 2-ethoxyethyl triflate 25 g of ethoxyethanol was placed in a round bottom flask provided with a stirrer piece therein, which was connected to a nitrogen bubbler to replace the air in the flask by dry nitrogen. 141 ml of methylene chloride was added and 33 ml of 2,6-lutidine was further added, followed by cooling down to −10 to 0° C., dropping 57 ml of trifluoromethanesulfonic acid anhydride in one hour and continuing agitation under the cooling conditions for one hour. 100 ml of distilled water was added to the reaction solution, and an organic phase was separated, washed with 100 ml of distilled water and dried with anhydrous sodium sulfate, followed by removing the sodium sulfate by filtration and distilling off the solvent under reduced pressure. The resulting residue was distilled under a reduced pressure of 150 Pa at 30° C. to obtain 57 g of a 2-ethoxyethyl triflate fraction.

(2) Preparation of o-(2-ethoxyethyl)-rapamycin 25 g of rapamycin was placed in a round bottom flask provided with a stirrer piece therein and a condenser was connected at the upper portion of the flask, followed by connection with a nitrogen bubbler and replacing the air in the flask by dry nitrogen. 88 ml of methylene chloride was added for dissolution and 250 ml of N,N-diisopropylethylamine was further added. Thereafter, while vigorously agitating, 49 g of the 2-ethoxyethyl triflate prepared in (1) above was added, followed by continuing agitation on an oil bath at 60° C. for one hour and 20 minutes. The mixture was diluted with 1.6 liters of ethyl acetate and washed successively with 2 liters of 1N hydrochloric acid, 2 liters of deionized water and 1.6 liters of a saturated saline solution. The resulting ethyl acetate phase was separated, to which 150 g of anhydrous sodium sulfate was added, followed by agitation for 20 minutes. After removal of the sodium sulfate by filtration, the solution was concentrated and evaporated to dryness by means of a rotary evaporator, and the resulting residue was purified by means of a column chromatograph having a silica gel bed with a diameter of 10 cm and a height of 100 cm (normal phase chromatograph). For an eluent, ethyl acetate/n-hexane (1:1, v/v), ethyl acetate/n-hexane (3:2, v/v) and ethyl acetate/n-hexane (7:3, v/v) were successively passed to collect and concentrate a fraction of the main product, followed by vacuum drying in a desiccator. 15.5 g of an amorphous purified product (o-(2-ethoxyethyl)-rapamycin) was obtained.

Subsequently, 3 g of above-described amorphous purified product is divided into three, i.e., 1 g each, and each portion is purified with reverse phase chromatograph under the conditions below.

(Conditions of Reverse Phase Chromatograph)
  Column size: 5 cm in diameter×25 cm in length
  Stationary phase: YMC GEL ODS-A, with a particle size of 20 μm and a pore size of 12 nm (made by YMC Co., Ltd.) A modification group modifying the stationary phase was an octadecyl group.
  Infusion fluid: 1 g of a starting material dissolved in 100 ml of 50 vol % of acetonitrile/50 vol % of deionized water
  Eluent: 75 vol % of acetonitrile/25 vol % of deionized water
  Flow rate: 100 ml/minute • Detection: UV 278 nm
  Column temperature: room temperature Using the reverse phase chromatograph, a main peak fraction eluted in a retention time of 20 to 30 minutes was collected. All the main peak fractions corresponding to three cycles of the purification were combined together, from which the solvent was removed to obtain 2.2 g of amorphous o-(2-ethoxyethyl)-rapamycin (40-0-[(2'-ethoxy)ethyl]rapamycin).

(3) Measurement of Purity

Next, the o-(2-ethoxyethyl)-rapamycin obtained by the reverse phase chromatograph was analyzed according to liquid chromatography under the following conditions to calculate a purity. The resulting chromatogram is shown in FIG. 1.

(Conditions of Liquid Chromatography)
Column: Zorbax SB-C18 with 4.6 mm in diameter×25 cm in length (made by Agilent Technologies Co., Ltd.)
Eluent: 70 vol % of acetonitrile/30 vol % of deionized water
Infusion dose: 10 uL (10 mg of a sample dissolved in 20 ml of acetonitrile)
Flow rate: 2.0 ml/minute • Analysis time: 1 hour
Detection: UV 278 nm • Column temperature: 40° C.
Calculation of purity (%): (peak area of o-(2-ethoxyethyl)-rapamycin×100)/(sum of all peak areas)

As a result of the calculation, the purity of o-(2-ethoxyethyl) rapamycin was found to be 99.7%.

Example 2

In the same manner as in Example 1 except that the conditions of the reverse phase chromatograph were changed as indicated below, o-(2-ethoxyethyl)-rapamycin was prepared.

(Conditions of Reverse Phase Chromatograph)
Column size: 5 cm in diameter×25 cm in length
Stationary phase: YMC GEL ODS-A, with a particle size of 20 μm and a pore size of 12 nm (made by YMC Co., Ltd.) A modification group modifying the stationary phase was an octadecyl group.
Infusion fluid: 1 g of a starting material dissolved in 100 ml of 50 vol % of methanol/50 vol % of deionized water
Eluent: 75 vol % of methanol/25 vol % of deionized water
Flow rate: 100 ml/minute • Detection: UV 278 nm • Column temperature: room temperature A main peak fraction eluted in a retention time of 20 to 30 minutes was collected. All main peak fractions corresponding to three cycles of the purification were combined, from which the solvent was removed to obtain 1.8 g of amorphous o-(2-ethoxyethyl)-rapamycin. The thus obtained o-(2-ethoxyethyl)-rapamycin was analyzed by liquid chromatography under conditions indicated in Example 1 to calculate a purity thereof, revealing that the purity of the o-(2-ethoxyethyl)-rapamycin was at 99.5%.

Example 3

In the same manner as in Example 1 except that the conditions of the reverse phase chromatograph were changed as indicated below, o-(2-ethoxyethyl)-rapamycin was prepared.

(Conditions of Reverse Phase Chromatograph)
Column size: 5 cm in diameter×25 cm in length
Stationary phase: YMC GEL C4, with a particle size of 20 μm and a pore size of 12 nm (made by YMC Co., Ltd.) A modification group modifying the stationary phase was a butyl group.
Infusion fluid: 1 g of a starting material dissolved in 100 ml of 50 vol % of acetonitrile/50 vol % of deionized water
Eluent: 75 vol % of acetonitrile/25 vol % of deionized water
Flow rate: 100 ml/minute • Detection: UV 278 nm • Column temperature: room temperature A main peak fraction dissolved out in a retention time of 27 to 40 minutes was collected. All main peak fractions corresponding to three cycles of the purification were combined, from which the solvent was removed to obtain 1.9 g of amorphous o-(2-ethoxyethyl)-rapamycin. The thus obtained o-(2-ethoxyethyl)-rapamycin was analyzed by liquid chromatography under conditions indicated in Example 1 to calculate a purity thereof, revealing that the purity of the o-(2-ethoxyethyl)-rapamycin was at 99.4%.

Example 4

2.2 g of o-(2-ethoxyethyl)-rapamycin obtained in Example 1 was dissolved in 10 ml of methanol, followed by dropping in 80 ml of agitated, deionized water. The resulting precipitated solid was filtered and washed with a small amount of water, followed by drying under reduced pressure at room temperature for 15 hours. 2.0 g of a white powder was obtained. The resulting white powder was analyzed by liquid chromatography under conditions indicated in Example 1 to calculate a purity thereof, revealing that the purity of o-(2-ethoxyethyl)-rapamycin was at 99.8%.

Comparative Example 1 o-(2-ethoxyethyl)-rapamycin was prepared in the same manner as in Example 1 except that the reverse phase chromatograph was not used for purification, thereby obtaining 15.5 g of an amorphous purified product (o-(2-ethoxyethyl)-rapamycin). The thus obtained o-(2-ethoxyethyl)-rapamycin was analyzed by liquid chromatography to calculate a purity thereof, revealing that the purity of the o-(2-ethoxyethyl)-rapamycin was at 95.2%.

Figure 2:
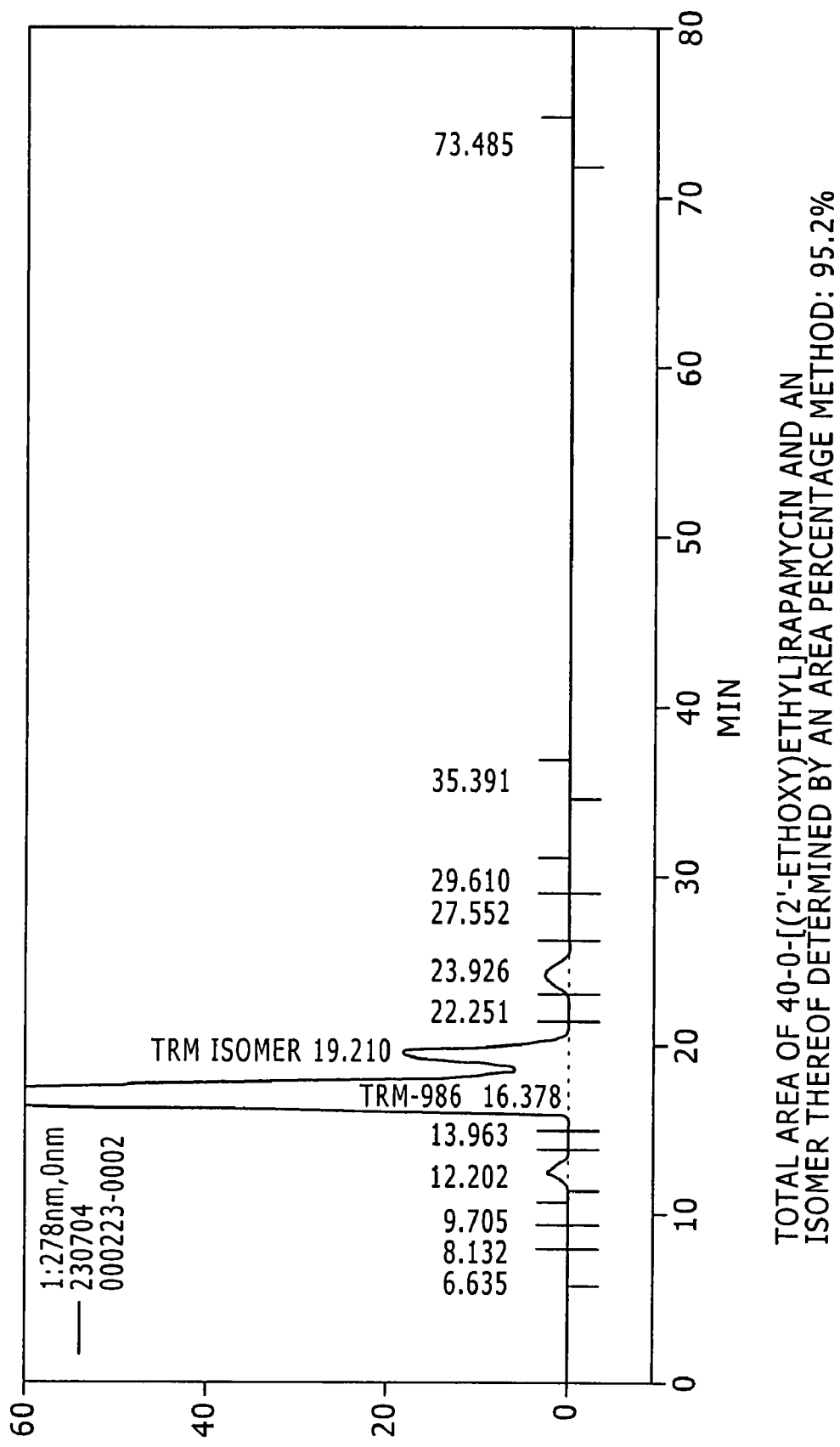
FIG. 2 is a chromatogram of a product obtained in Comparative Example 1.

The chromatogram of Comparative Example 1 is shown in FIG. 2. The peak in the vicinity of the retention time of 17 minutes corresponds to an intended product and the peak in the vicinity of 19.5 minutes corresponds to an isomer of the intended product, and the total area of these products was calculated as derived from the intended product. Other peaks correspond all to those derived from impurities.

What is claimed is:
1. A process for preparing a compound represented by formula (1), comprising the steps of:
(a) reacting rapamycin with an alkyl triflate;
(b) purifying the resulting reaction product with a normal phase chromatograph after (a); and
(c) further purifying a purified product, which has been purified with the normal phase chromatograph, with a reverse phase chromatograph after (b);

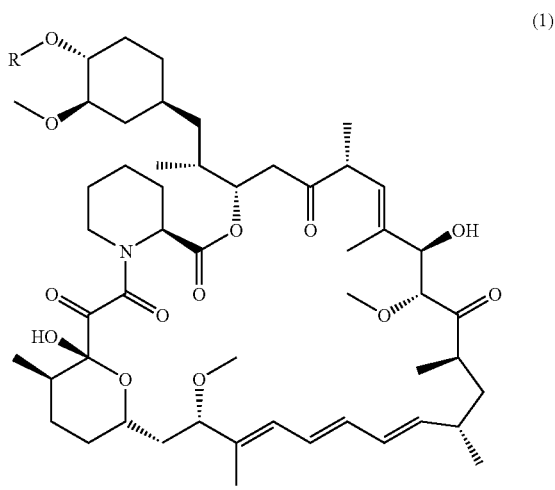

(1)

wherein R represents an alkyl, arylalkyl, hydroxyalkyl, alkoxyalkyl, acyloxyalkyl, aminoalkyl, alkylaminoalkyl, alkoxycarbonylaminoalkyl, acylaminoalkyl, or aryl, and wherein a stationary phase used in the reverse phase chromatograph is formed from a silica gel having a particle size in a range from 10 to 50 μm.

2. The process for preparing the compound according to claim 1, wherein the stationary phase used in the reverse phase chromatograph is modified with at least one selected from the group consisting of an alkyl group, a phenyl group, and an alkylsilyl group.

3. The process for preparing the compound according to claim 2, wherein the alkyl group is at least one member selected from the group consisting of a butyl group, an octyl group and an octadecyl group.

4. The process for preparing the compound according to claim 1, wherein an eluent used in the reverse phase chromatograph is a mixed solution obtained by mixing 10 to 50 vol % of water relative to at least one organic solvent selected from the group consisting of acetonitrile, methanol, ethanol and propanol.

5. The process for preparing the compound according to claim 4, wherein the organic solvent is acetonitrile or methanol.

6. The process for preparing the compound according to claim 5, wherein a ratio of the water to the acetonitrile or methanol ranges from 20 to 35 vol %.

7. The process for preparing the compound according to claim 1, wherein an infusion fluid used in the reverse phase chromatograph is a mixed solution obtained by mixing 40 to 60 vol % of water relative to at least one organic solvent selected from the group consisting of acetonitrile, methanol, ethanol and propanol.

8. The process for preparing the compound according to claim 1, wherein a product purified by the normal phase chromatograph in an amount of 1 to 4 g per 1.0 liter of a column head capacity is provided for separation in the reverse phase chromatograph.

9. The process for preparing the compound according to claim 1, wherein after the preparation of the compound according to the process recited in claim 1, the resulting derivative is subsequently charged into a mixed solvent containing at least one solvent miscible with water and water, or is dissolved beforehand in at least one solvent miscible with water and charged into water or a mixed solvent containing water, thereby causing the product to be precipitated.

10. The process for preparing the compound according to claim 9, wherein the solvent miscible with water is used at a ratio by weight of 2 to 10 relative to the compound.

11. The process for preparing the compound according to claim 9, wherein the water is used at a ratio by weight of not less than 10 relative to the compound.

12. The process for preparing the compound according to claim 9, wherein the solvent miscible with water is an alcohol.

13. The process for preparing the compound according to claim 12, wherein the alcohol is methanol.

14. The process for preparing the compound according to claim 9, wherein the precipitation is performed such that the compound is dissolved beforehand in a solvent containing at least one solvent miscible with water, followed by charging into water or a mixed solvent of at least one solvent miscible with water and water.

15. The process for preparing the compound according to claim 1, wherein a purity of the further purified product is not lower than 99%.

* * * * *